United States Patent [19]

Peters

[11] 4,299,920
[45] Nov. 10, 1981

[54] BIOLOGICAL RECEPTACLE

[76] Inventor: J. Hinrich Peters, Lughauser Str. 70, 5064 Rosrath-Hoffnungsthal, Fed. Rep. of Germany

[21] Appl. No.: 111,759

[22] Filed: Jan. 14, 1980

[30] Foreign Application Priority Data

Jan. 19, 1979 [DE] Fed. Rep. of Germany ....... 2902026

[51] Int. Cl.$^3$ .......................... C12M 3/04; C12M 3/00
[52] U.S. Cl. ................................... 435/285; 435/284; 435/299; 435/300; 435/301
[58] Field of Search ............... 435/284, 285, 286, 240, 435/241, 297, 298, 299, 300, 301

[56] References Cited

U.S. PATENT DOCUMENTS 2,971,892  2/1961  Carski ................................ 435/298
3,745,091  7/1973  McCormick ..................... 435/301 X
3,928,142  12/1975  Smith .............................. 435/299 X

FOREIGN PATENT DOCUMENTS 2157150  1/1973  Fed. Rep. of Germany .

Primary Examiner—Robert J. Warden
Attorney, Agent, or Firm—Sprung, Felfe, Horn, Lynch & Kramer

[57] ABSTRACT

A receptacle for cell cultures or biological tests comprising a base plate, and a wall member joined in detachable and liquid-tight manner to the base plate, the base plate and wall defining at least one chamber, at least that portion of the wall adjacent the base plate consisting of a noncytotoxic elastomeric synthetic material adhering to the base plate.

11 Claims, 6 Drawing Figures

BIOLOGICAL RECEPTACLE

BACKGROUND OF THE INVENTION

The invention relates to a biological receptacle for cell cultures or biological tests which has a base plate that is joined in detachable and liquid-tight manner to the side walls of the receptacle, the base plate and side walls enclosing at least one chamber, and the side walls forming a wall section, a cover being optionally provided for the chamber or chambers.

A receptacle of this type is known from German patent application DAS No. 2,157,150. There the base plate is joined to the wall section by means of an adhesive gasket which is bonded to the base plate and fits into grooves in the wall section. The base plate serves as a solid substrate for attachment of living cells of higher organisms which are cultivated under sterile conditions in suitable culture media in a cell culture. In cell biology it is often necessary for cells grown on a surface to be analyzed outside the culture, under the microscope, by biochemical methods or by methods for determination of the uptake of radioactivity. On completion of cultivation, the wall section of this receptacle is therefore manually detached from the base plate. However, the gasket bonded to the base plate remains stuck to it and must be scraped off, which is a nuisance. This is why practically only base plates made of glass are suited for this application. Such plates, however, are not an appropriate substrate for attachment of all types of cells. Moreover, because of the gasket which has to be bonded to it, such a receptacle is not easy to produce and can be used only once.

SUMMARY OF THE INVENTION

The present invention thus has as its object to provide a receptacle of the type described above that is very much easier to produce and whose base plate can readily be detached with the cell culture disposed thereon and reused without additional measures.

This object is accomplished in that at least the portion of the wall section which is adjacent to the base plate consists of a noncytotoxic elastomeric synthetic material which adheres to the base plate in liquid-tight manner.

Since the wall section is joined to the base plate only by adhesion, these two parts can readily be separated from each other. There is no need to provide a gasket; the base plate and the wall section need merely be brought into contact with each other and possibly be pressed against each other in order to produce adhesion. Moreover, the wall section can be reused as a unit after having been washed in a solution of a nontoxic detergent, rinsed with distilled water, and sterilized by autoclaving, for example.

The wall section may also be of two-layer construction, with the layer facing the base plate consisting of the noncytotoxic elastomeric synthetic material which adheres to the base plate in liquid-tight manner. The surface of the wall section facing away from the base plate may be of analogous composition. However, the entire wall section may be made of said synthetic material. Moreover, in the case of receptacles of greater extension with numerous chambers, there may be embedded in the wall section a reinforcement plate of an essentially rigid material.

The adhesive surface of the wall section may be flat and smooth, or it may be concave. Adhesion is also possible when the adhesive surface of the wall section is not perfectly smooth but has a satin finish, in other words, is rough on the microscale. Moreover, the adhesive surface may be interrupted by groove- or cup-like depressions in order to compensate for slight differences in the thermal expansion behavior of the two adhering materials.

The wall section is preferably made of a hydrophobic synthetic material, and in particular of silicone rubber.

Other non-cytotoxic elastomeric synthetic materials are those of the following groups:

1. Polyvinylchloride with high molecular plasticizers, especially ethylene-vinylacetate-copolymers, wherein the vinylacetate content may amount up to 90% by weight. This makes the plastic very soft. The hydrophobic properties can be regulated by varying the ethylene content of the plasticizer.
2. Polyurethane-elastomers with varying alcohol-moieties.
3. Polyvinylidene-chloride.
4. Methyl-rubber or chlorinated rubber, which are hydrophobic and the properties of these rubber can be regulated by the addition of fillers, stabilizers, silicone-oil or other lubricants.
5. Fluorocarbon elastomers, especially those which are not perfluorated but partially chlorinated.

The base plate may be made of glass since glass, too, will adhere to silicone rubber. Preferably, however, the base plate is made of a synthetic material which has adhesion for the wall section and at the same time forms a good substrate for cell cultures. Suitable are, for example, bendable plates of polyurethane, polystyrene or the like of a thickness of about 0.5 mm. These plastics are compatible with cells and will form a base plate suitable for cell cultures.

However, a filter plate made of polycarbonate, for example, whose pores permit the passage of molecules, particles or cell proliferations might also be used.

The chambers may taper toward the base plate, and the height of the wall section or of the chambers, respectively, may range from 0.1 to 20 mm, and more particularly from 2 to 10 mm.

Moreover, the receptacle may be provided with a loose-fitting cover, particularly one having an overlapping edge. However, the cover may also be held to the wall section by adhesion.

BRIEF DESCRIPTION OF THE DRAWINGS

The invention will now be explained in greater detail with reference to the accompanying drawings illustrating several embodiments and giving the dimensions, in mm, thereof.

FIGS. 1b, 2b and 3b are cross-sectional views of FIGS. 1a, 2a and 3a.

DETAILED DESCRIPTION OF THE INVENTION

Figure 1A:
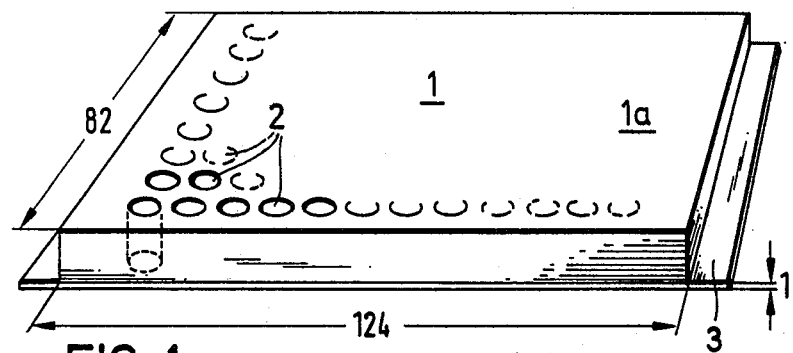
FIGS. 1a, 2a and 3a are perspective views of three different embodiments of a biological receptacle in accordance with the invention.
Figure 1B:
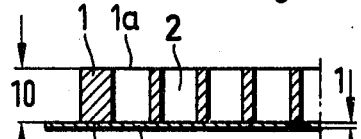

The biological receptacle shown in FIGS. 1a and 1b consists of a wall section 1 of relatively large extension and having a plurality of cylindrical holes which extend in a desired pattern from the top 1a to the underside 1b of the wall section 1 and are open at both ends. The wall section 1 adheres to a base plate 3 so that the holes are sealed in liquid-tight manner on their underside by the base plate 3, a plurality of chambers 2 being formed in this way. The base plate 3 projects on two opposite sides beyond the wall section 1.

Figure 2A:
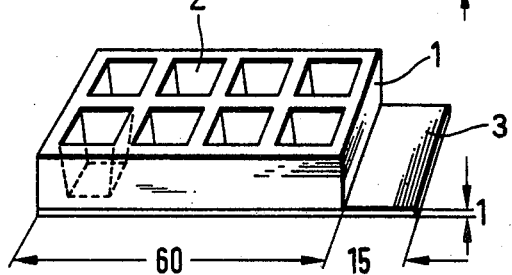
Figure 2B:
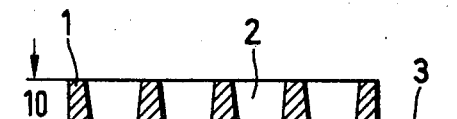

In the embodiment shown in FIGS. 2a and 2b, the chambers 2 are formed by square openings in the wall section 1 which taper toward the base plate 3.

Figure 3A:
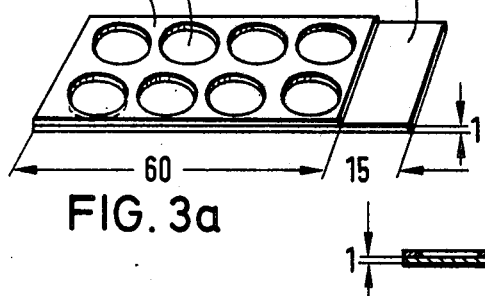
Figure 3B:
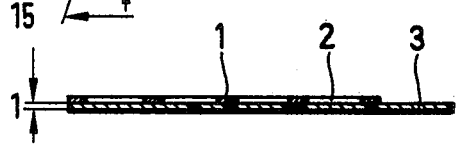

In the embodiment shown in FIGS. 3a and 3b, the wall section 1 is of small height, and the chambers 2 therefore are shallow.

The base plates 3 are flexible and may be made of polystyrene, polyethylene, polypropylene, polycarbonate and fluorinated polymerized hydrocarbons. However, glass microscope slides may also be used.

Moreover, the base plate 3 may also be formed by dialyzing and filter membranes which, depending on the size of their pores, permit molecules, particles, cell projections, or cells to pass through them. For this purpose, the receptacle is placed in an appropriate liquid which is able to diffuse through the pores to the interior of the chambers 2.

The base plate 3 may be provided with test substances such as test reagents, antiserums, virus preparations and the like even before it is joined to the wall section 1. These substances are allowed to dry on discrete areas of the base plate 3 corresponding to the grid pattern of the chambers 2. In this way, the standardized testing of reagents for their effect on cells and other biological preparations is facilitated and its cost is brought down since such base plates 3 are easier and cheaper to store, package and handle than similarly prepared one-piece cell-culture receptacles.

For use, wall section 1 and base plate 3 are assembled, which may be done with the aid of a frame permitting the wall section 1 and the base plate 3 to be precisely aligned with each other. The chambers 2 are then filled with the suspension of cells to be cultivated. The cells may then be experimentally manipulated as is the practice with the usual cultures. The chambers 2 may either be placed in a sterile petri dish and cultivated under standard conditions, with the cover of the petri dish in place, or provided with a cover of their own. The cover may fit loosely and be provided with vent studs and an overlapping edge, or it may be held to the wall section 1 by adhesion and thus close the chamber 2 in the same way that the base plate 3 is closed on its underside. In this case, the chamber 2 may be cultivated as a closed system. For biological tests, the receptacle may be used for the testing of noncellular reactions, such as agglutination reactions with latex beads or with killed cells.

On completion of cultivation, the base plate 3 may readily be separated from the wall section 1. The cells may be fixed either before or after such separation. If unattached cells or products of color or agglutination reactions are to be retained on the base plate 3 and preserved, they must first be dried with an appropriate fixative such as a concentrated protein solution.

However, unfixed attached cells may continue to be cultivated on the base plate 3 even after removal of the wall section 1, by placing the base plate 3 into a culture dish with culture medium.

The base plate 3 with the cell culture may form a microscope slide or may be mounted on a glass slide. Evaluation by means of histological staining, histochemical reactions or immunofluorescence is possible.

After the cultivated cells have been radioactively labeled, a microscope autoradiography may be performed in which photographic silver particles will form over the site of incorporation of the radioactive substance.

Radioactively labeled cells on the base plate 3, particularly on toluene-insensitive transparent materials, may be tested for their radioactivity by scintillation counting. Particularly well suited for this purpose are plastic plates which can be cut up into the various culture areas, which then are measured individually.

Moreover, cells for electron microscopy may be embedded on plastic plates serving as base plates 3 and cut ultrathin.

An embodiment of the receptacle according to FIGS. 1a and 1b is particularly well suited for adoption of the microtitration system, for which a great many accessories are available. These permit the pipetting of large series and the collecting of culture supernatants or suspended cells for further analysis.

For tests to be performed with a scintillation counter, base plates 3 made of a toluene-resistant plastic may be cut either with a scissors or with a die into appropriate fields, i.e. squares which then are allowed to drop directly into a glass dish filled with liquid scintillator which has been placed under them.

On completion of the tests, the subdivided dried base plate 3 with the cell culture disposed thereon may be preserved compactly in foil or sheet form.

Moreover, the cells in the individual chambers 2 may be cultivated and radioactively labeled and on completion of cultivation the base plate 3 may be left on the wall section 1 and an additional wall section 1 may be set onto and properly aligned with the base plate 3, formed by a filter membrane, from the other side. A wash liquid may then be introduced into this combination of two wall sections 1 and a base plate 3 and simultaneously drawn off downwardly. By proper choice of wash liquid, the suspended cells may be retained on the base plate 3, formed by a filter membrane, opened up and extracted as desired so that ultimately the insoluble material remains on the base plate 3. The latter may then be removed and the individual samples subjected to scintillation counting.

It will be appreciated that the instant specification and claims are set forth by way of illustration and not limitation, and that various modifications and changes may be made without departing from the spirit and scope of the present invention.

What is claimed is:

1. A receptacle containing a test medium such as a cell culture or biological specimen consisting of a base plate and wall member, the wall member having a flat smooth bottom self-adhering to the base plate in liquid-tight manner, the wall member being formed of noncytotoxic hydrophobic elastomeric synthetic material compatible with the test medium and defining with the base plate a plurality of independent chambers, and a plurality of test media in the independent chambers.

2. A receptacle according to claim 1, wherein the synthetic material is a silicone rubber.

3. A receptacle according to claim 1, wherein the chamber tapers toward the base plate.

4. A receptacle according to claim 1, wherein the height of the chamber ranges from 0.1 to 20 mm.

5. A receptacle according to claim 1, wherein the base plate is made of a plastic material compatible with cells.

6. A receptacle according to claim 1, wherein the base plate includes pores permitting the passage there-through of molecules, particles, cells, or cell projections.

7. A receptacle according to claim 1, including a loose-fitting cover, having an overlapping edge.

8. A receptacle according to claim 1, including an adhesive cover.

9. A receptacle according to claim 1, wherein the wall member has an adhesive surface which has a satin finish and/or is interrupted by groove- or cup-like depressions.

10. A receptacle according to claim 1, wherein test substances are applied to the base plate in a pattern corresponding to the grid of the chambers of the wall member.

11. A receptacle according to claim 1, in combination with a frame permitting the assembly of wall and base plate in alignment with one another.

* * * * *